United States Patent
Sayani et al.

(10) Patent No.: US 11,896,384 B2
(45) Date of Patent: Feb. 13, 2024

(54) WEARABLE MATERNITY SENSOR DEVICE

(71) Applicant: The Aga Khan University, Karachi (PK)

(72) Inventors: Saleem Sayani, Wynnewood, PA (US); Muhammad Abdul Muqeet, Karachi (PK); Hafiz Imtiaz Ahmed, Karachi (PK); Naeem Sheikh, Karachi (PK); Sannan Ahmed Qureshi, Karachi (PK); Nadeem Zuberi, Karachi (PK)

(73) Assignee: The Aga Khan University, Karachi (PK)

( * ) Notice: Subject to any disclaimer, the term of this patent is extended or adjusted under 35 U.S.C. 154(b) by 530 days.

(21) Appl. No.: 16/696,721

(22) Filed: Nov. 26, 2019

(65) Prior Publication Data

US 2021/0106273 A1    Apr. 15, 2021

(30) Foreign Application Priority Data

Oct. 11, 2019 (PK) ..................... 679/2019

(51) Int. Cl.
| | |
|---|---|
| *A61B 5/00* | (2006.01) |
| *G16H 20/30* | (2018.01) |
| *G16H 40/67* | (2018.01) |
| *A61B 5/288* | (2021.01) |

(52) U.S. Cl.
CPC .......... *A61B 5/4362* (2013.01); *A61B 5/0022* (2013.01); *A61B 5/288* (2021.01); *A61B 5/6804* (2013.01); *A61B 5/6831* (2013.01); *A61B 5/7264* (2013.01); *A61B 5/746* (2013.01); *G16H 20/30* (2018.01); *G16H 40/67* (2018.01); *A61B 2560/0223* (2013.01); *A61B 2562/16* (2013.01)

(58) Field of Classification Search
CPC ..... A61B 5/4362; A61B 5/0022; A61B 5/288; A61B 5/6804; A61B 5/6831; A61B 5/7264; A61B 5/746; A61B 2560/0223; A61B 2562/16; A61B 2562/02; A61B 5/0011; G16H 20/30; G16H 40/67; G16H 50/30

See application file for complete search history.

(56) References Cited

U.S. PATENT DOCUMENTS

| | | | | |
|---|---|---|---|---|
| 2014/0228653 | A1* | 8/2014 | Kiraly | A61B 8/02 600/382 |
| 2014/0276239 | A1* | 9/2014 | Subramaniam | A61B 5/746 600/595 |
| 2016/0058363 | A1* | 3/2016 | Hayes-Gill | A61B 5/742 600/588 |
| 2016/0270670 | A1* | 9/2016 | Oz | A61B 5/282 |

(Continued)

*Primary Examiner* — Alex M Valvis
*Assistant Examiner* — Nidhi N Patel
(74) *Attorney, Agent, or Firm* — Fish & Richardson P.C.

(57) ABSTRACT

A sensor device is described that includes a dry electrode, a pressure sensor, and a communication apparatus. The dry electrode is configured to be placed adjacent to a belly of a pregnant patient. The pressure sensor is coupled to the dry electrode to sense pressure within the belly. The sensed pressure indicates counts of physiological activities of a fetus within the pregnant patient over a period of time. The communication apparatus is coupled to the pressure sensor and the dry electrode. The communication apparatus is configured to transmit data characterizing the counts of the plurality of physiological activities to a cloud computing server for generating an assessment of health of the fetus.

18 Claims, 11 Drawing Sheets

(56) References Cited

U.S. PATENT DOCUMENTS

| | | | |
|---|---|---|---|
| 2016/0374608 A1* | 12/2016 | Dugan | A61B 5/746 |
| | | | 600/301 |
| 2017/0127997 A1* | 5/2017 | Hyde | A61B 5/746 |
| 2017/0273664 A1* | 9/2017 | Baym | A61B 8/485 |
| 2017/0367643 A1* | 12/2017 | Falk | A61B 5/318 |
| 2018/0353142 A1* | 12/2018 | Shah | A61B 5/1107 |
| 2018/0368753 A1* | 12/2018 | Yin | A61B 5/4362 |

\* cited by examiner

WEARABLE MATERNITY SENSOR DEVICE

CROSS-REFERENCE TO RELATED APPLICATION

This disclosure claims priority to Pakistan Patent Application No. 679/2019, entitled "Wearable Maternity Sensor Device" and filed on Oct. 11, 2019, the entire contents of which are incorporated herein by reference.

TECHNICAL FIELD

The subject matter described herein relates to a wearable maternity sensor device that communicates with a cloud computing server to generate, on a web-based application accessible to a clinician, a clinical report indicating assessment of health of a fetus within a patient wearing the sensor device.

BACKGROUND

Throughout the three trimesters of pregnancy, monitoring of the fetus within a patient (i.e., mother) is important to ensure that the fetus remains healthy. For example, such monitoring can indicate whether the fetus is under stress. However, such monitoring is often performed only at a clinic, and thus fails to diagnose potential health issues between such clinical visits by the patient. There, accordingly, exists a need for a device that permits frequent and convenient monitoring of the heath of the fetus to ensure that the patient and the fetus remain healthy.

SUMMARY

In one aspect, a sensor device is described that includes a dry electrode, a pressure sensor, and a communication apparatus. The dry electrode is configured to be placed adjacent to a belly of a pregnant patient. The pressure sensor is coupled to the dry electrode to sense pressure within the belly. The sensed pressure indicates counts of physiological activities of a fetus within the pregnant patient over a period of time. The communication apparatus is coupled to the pressure sensor and the dry electrode. The communication apparatus is configured to transmit data characterizing the counts of the plurality of physiological activities to a cloud computing server for generating an assessment of health of the fetus.

In some variations, one or more of the following can additionally be implemented either individually or in any suitable combination. The sensor can further include a top cover, a disc, a circular clip, a spring, a top bowl, a bottom bowl, and a bottom cover. The top cover can include a cavity and one or more clips. The circular clip can couple with the cavity. A bottom surface of the disc can float with respect to the pressure sensor. A circular edge of the disc can prevent the pressure sensor from dismantling. A top surface of the top bowl can have a projection that is configured to couple with a corresponding cavity in a lower surface of the pressure sensor. The bottom cover can couple with the one or more clips. The bottom cover can include an opening through which the dry electrode can pass.

The cloud computing server can generate a report that includes the assessment of the health of the fetus. The report can be a web-based report that can be updated in real-time. The cloud computing server can include an application programming interface, one or more controllers, and or more web modules. The application programming interface can receive data characterizing the counts of the plurality of physiological activities. The one or more controllers can be communicatively coupled to the application programming interface. The one or more controllers can compute, using the counts of the plurality of physiological activities, the assessment of the health of the fetus. The one or more web modules can be coupled to the application programming interface. The one or more web modules can generate data characterizing a web-based report that includes the assessment of the health, The one or more controllers can transmit the data characterizing the web-based report to a computer on which accurate authentication information for accessing the report is input.

The one or more controllers can store assessment in at least one database communicatively coupled to the one or more controllers. The one or more web modules can retrieve the assessment from the at least one database to generate the web-based report. The cloud computing server can further include one or more software development kits that can modify a web application that displays the web-based report.

In another aspect, a controller within a sensor device can commence, in response to pressing of a button on the sensor device, sensing of physiological activities of a fetus from a belly of a pregnant patient. The controller can calibrate one or more sensors within the sensor device based on historical data stored in a cloud database communicatively coupled to the controller. The controller can determine counts of the physiological activities per unit time once the one or more sensors have been calibrated. The controller can transmit the counts to a cloud computing server for assessment of fetal health for the pregnant patient.

In some variations, one or more of the following can additionally be implemented either individually or in any suitable combination. The cloud computing server can generate a web-based report that comprises the assessment of fetal health for the pregnant patient. The web-based report can be updated in real-time. The web-based report can be updated at time-intervals determined based on computing resources of the cloud computing server. The sensor device can be worn on a maternity belt. Alternately, the sensor device can be a part of clothing of the pregnant patient. The sensor device is portable.

In yet another aspect, a cloud computing server is described that can include an application programming interface, one or more controllers, and one or more web modules. The application programming interface can receive, from a sensor device, data characterizing counts of physiological activities of a fetus within a pregnant patient over a period of time. The one or more controllers can be communicatively coupled to the application programming interface. The one or more controllers configured to compute, using the counts, an assessment of health of the fetus. The one or more web modules can be coupled to the application programming interface. The one or more web modules can generate data characterizing a web-based report that indicates the assessment of the health of the fetus. The one or more controllers configured to transmit the data characterizing the web-based report to a computer on which accurate authentication data for accessing the report is input.

In some variations, one or more of the following can additionally be implemented either individually or in any suitable combination. The cloud computing server can further include at least one database communicatively coupled to the one or more controllers. The one or more controllers can store the assessment of the health of the fetus in the at least one database. The one or more web modules can retrieve the assessment of the health of the fetus from the at least one database to generate the web-based report.

The cloud computing server can further include one or more software development kits configured to modify a web application that displays the web-based report. The authentication data can be one or more of: username, password, personal identification number (PIN), answer to a secret question, biometric identification, place of authentication, and time of authentication.

In another aspect, a system is described that includes a sensor device and a cloud computing server. The sensor device can include: a dry electrode configured to be placed adjacent to a belly of a pregnant patient; a pressure sensor coupled to the dry electrode to sense pressure within the belly to determine counts of physiological activities of a fetus within the pregnant patient over a period of time; and a communication apparatus coupled to the pressure sensor and the dry electrode. The cloud computing server can include: an application programming interface configured to receive, from the communication apparatus, data characterizing the counts of the physiological activities of the fetus over the period of time; one or more controllers communicatively coupled to the application programming interface, the one or more controllers configured to compute, using the counts of the physiological activities of the fetus, an assessment of health of the fetus; and one or more web modules coupled to the application programming interface, the one or more web modules configured to generate data characterizing a web-based report that indicates the health of the fetus, the one or more controllers configured to transmit the data characterizing the web-based report to a computer on which accurate authentication data for accessing the report is input.

In some variations, one or more of the following can additionally be implemented either individually or in any suitable combination. The sensor device can further include: a top cover comprising a cavity and two clips; a disc, a circular clip, and a spring, the circular clip configured to couple with the cavity, a bottom surface of the disc configured to float with respect to the pressure sensor, a circular edge of the disc preventing the pressure sensor from dismantling; a top bowl, a bottom bowl and the dry electrode, a top surface of the top bowl having a projection that is configured to couple with a corresponding cavity in a lower surface of the pressure sensor; and a bottom cover configured to couple with the two clips, the bottom cover comprising an opening through which the dry electrode is configured to pass.

Related methods, systems, devices, apparatuses, non-transitory computer program products, and articles of manufacture are also within the scope of this disclosure.

The subject matter described herein provides many advantages. For example, the sensor device is portable and wearable. Additionally, the simplistic structural design of the sensor device makes it easy to set-up (e.g., assemble, and then initiate functionality) and use. Furthermore, the sensor device is compact in size, and thus does not inhibit mobility of the patient. In addition, the sensor device captures data non-invasively, and without abrasion of the skin of the patient and without applying gels, fluids, or sticky and/or wet pads. Moreover, the sensor device communicates with the cloud computing server to generate a clinical report that the clinician can review remotely, thereby obviating the need for clinical visits when unnecessary. Further, the use of a cloud computing server is advantageous over a traditional server, as the cloud computing server permits a quick scalability by modification of current web services that generate the clinical report and/or addition of additional web services within a few seconds. Additionally, the clinical report is displayed only in response to the patient's clinician inputting authentication data for accessing the clinical report, thereby ensuring computational security of the clinical report, which in turn keeps patient data confidential.

The details of one or more variations of the subject matter described herein are set forth in the drawings and the description below. Other features and advantages of the subject matter described herein will be apparent from the description, drawings, and claims.

DESCRIPTION OF DRAWINGS

Like reference symbols in the various drawings indicate like elements.

DETAILED DESCRIPTION

Figure 1:
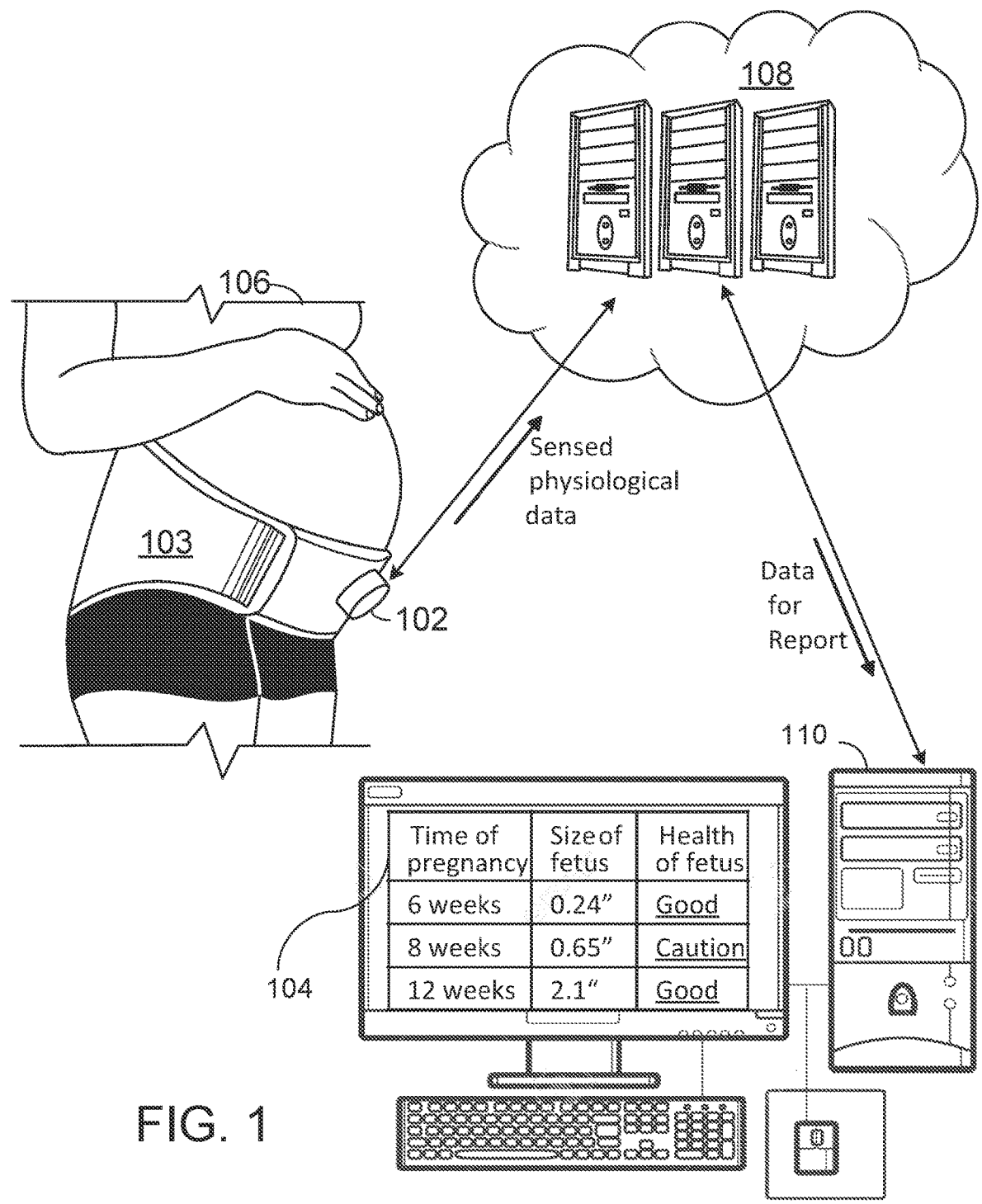
FIG. 1 illustrates a sensor device that communicates with a cloud computing server to generate, on a web-based application accessible to a clinician, a clinical report for assessment of health of a fetus within a patient wearing the sensor device, in accordance with some implementations of the current subject matter.

FIG. 1 illustrates a sensor device 102 being used to generate a clinical report 104 indicating fetal health of a fetus within a patient 106 wearing the sensor device 102 at various time points. The sensor device 102 is configured to communicate with a cloud computing server 108, which is configured to generate data for the report 104. The report 104 can be a restricted webpage that can be accessed by a clinician by providing user authentication data via any computer, such as the computer 110. The sensor device 102 is configured to be portable and worn by the patient 106. For example, the sensor device 102 is a part of a maternity belt 103. In other implementations, the sensor device 102 can be a part of the clothing of the patient 106. Structural details of the sensor device are described in detail below by FIGS. 2-7.

The sensor device 102 is communicatively coupled with the cloud computing server 108 via a communication network such as the internet. In alternate implementations, the sensor device 102 can be communicatively coupled with the cloud computing server 108 via any other communication network, which can be a wired network or a wireless network. The wireless network can be one or more of radio communication network, cellular network, satellite network, Wi-Fi network, ZIGBEE™ network, infrared network, microwave network, light-wave network, and any other communication network.

The cloud computing server 108 is communicatively coupled with the computer 110 via a communication network such as the internet. In alternate implementations, the cloud computing server 108 can be communicatively coupled with the computer 110 via any other communication network, which can be a wired network or a wireless network. The wireless network can be one or more of radio communication network, cellular network, satellite network, Wi-Fi network, ZIGBEE™ network, infrared network, microwave network, light-wave network, and any other communication network.

Figure 4:
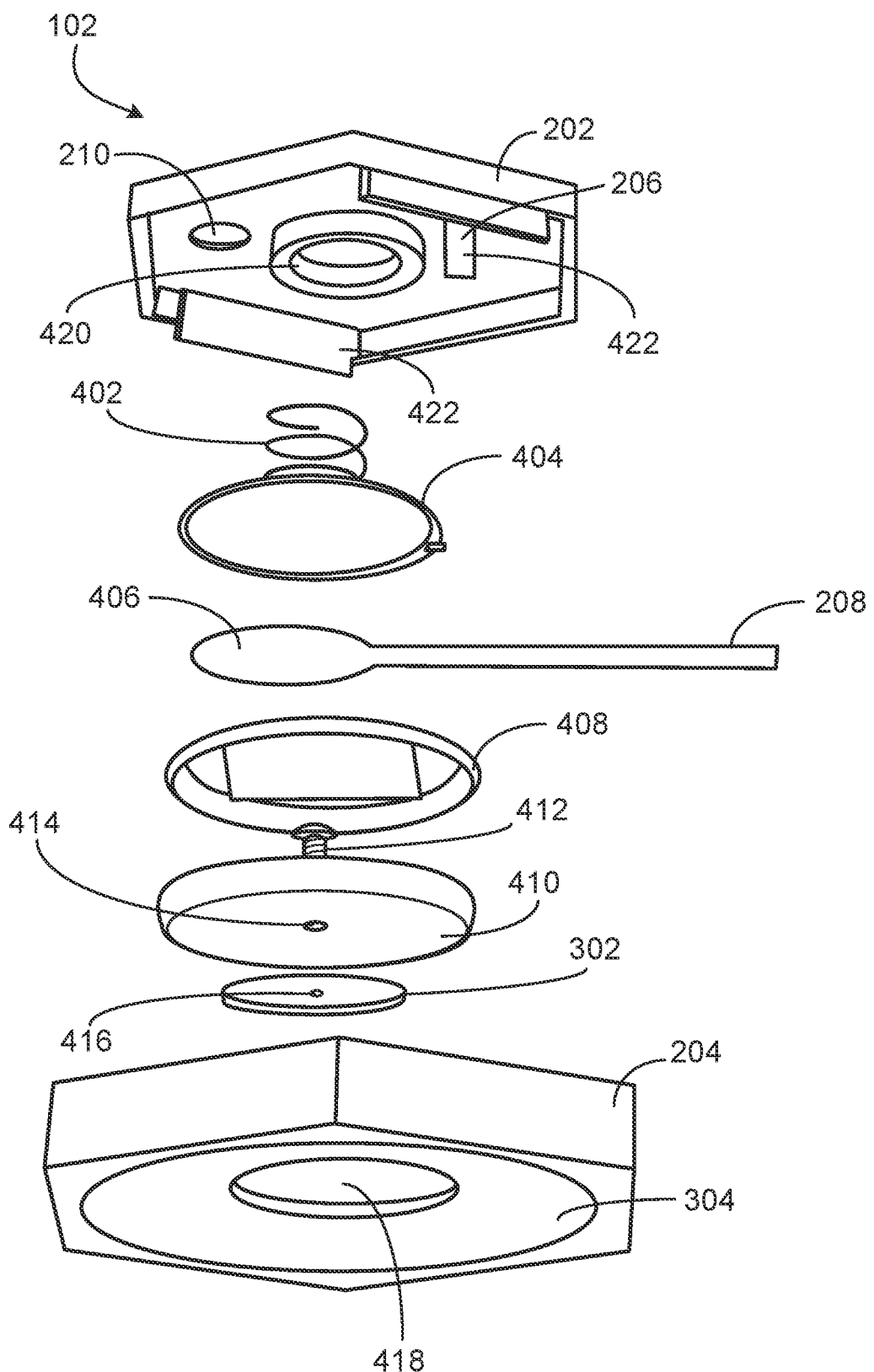
FIG. 4 illustrates an exploded view of the sensor device, in accordance with some implementations of the current subject matter.
Figure 5:
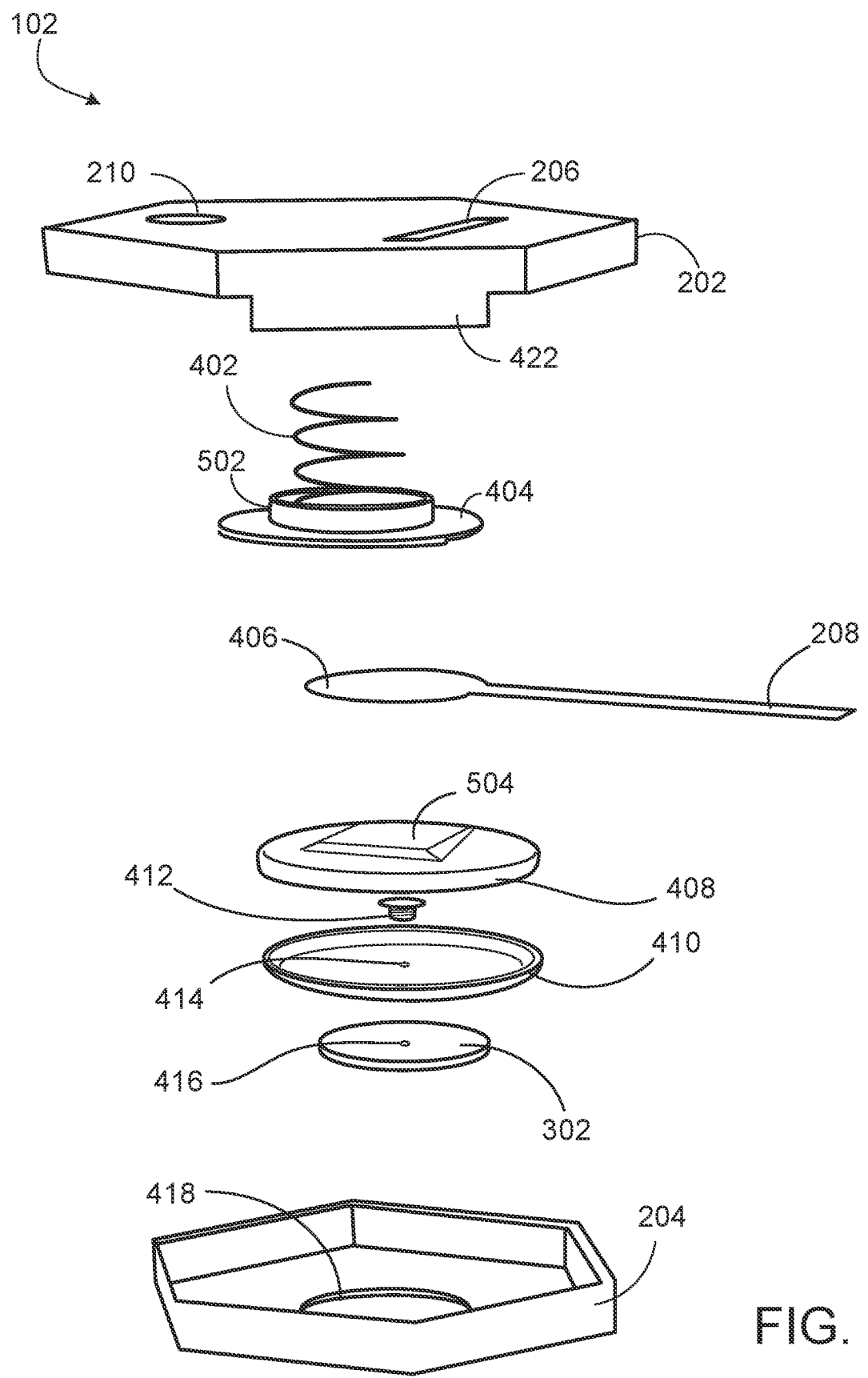
FIG. 5 illustrates another exploded view of the sensor device, in accordance with some implementations of the current subject matter.

The sensor device 102 has an electronic button that can be pressed by the patient 106 to activate the sensor device 102. Once activated, the sensor device 102 is first calibrated as follows. The sensor device 102, once placed adjacent to a lower abdominal region of the patient 106, begins sensing and measuring physiological activities—e.g., kicks, rolls, punches, jabs, any other fetal activity, and/or any combination thereof—of the fetus within the patient 106 to generate current measurements of physiological activities. The sensor device 102 has a pressure sensor—as shown in FIGS. 4 and 5 and discussed in further detail below with respect to those drawings—that is configured to differentiate between each physiological activity by the fetus. The measurements of the physiological activity can include an amount (e.g., number) of the above-mentioned physiological activity per unit time, which can be any time ranging from one minute to a few days. For purposes of calibration, smaller time units can help expedite the calibration process, but larger time units can provide more accuracy to the calibration.

The calibration process is now described. The sensor device 102 receives, from the cloud computing server 108, historical measurements of such physiological activities. The historical measurements can be measurements—stored in the cloud computing server 108—of the physiological activities earlier sensed and measured for the patient 106 during a similar stage in a previous pregnancy, or another patient who is in a similar stage in a current pregnancy. If there is no record available of measurements of the patient 106 or another patient, as noted above, in the cloud computing server 108, the sensor device 102 can retrieve, from the computing server 104, recommended (e.g., expected, as based on characteristics of the patient 106) values for historical measurements, as published by a standard body such as the World Health Organization or another entity. The sensor device 102 can compare the current measurements of the patient 106 with the historical measurements that were stored in the cloud computing server 108. The sensor device 102 can use this comparison to adjust, for example, the structural positioning of the sensors within the sensor device 102 so that the future measurements lie within a threshold amount of a mean (i.e., average) of the historical measurements. Such adjustment of structural positioning of the sensors is referred to as calibration.

The calibration can enhance accuracy by ensuring that the sensor device 102 is working properly, especially because the accuracy of the sensor device 102 can potentially degrade over time due to normal/expected usage. The configuring of the sensor device 102 to be calibrated prior to usage can improve the accuracy, and thus the product quality, of the sensor device 102.

Once the sensor device 102 is calibrated, the sensor device 102, when placed adjacent to a lower abdominal region of the patient 106, can continue to sense and measure physiological activities—e.g., kicks, rolls, punches, jabs, any other fetal activity, and/or any combination thereof—of the fetus within the patient 106 to generate current measurements of physiological activities. The measurements of a physiological activity can include an amount (e.g., number) of the above-mentioned physiological activity per unit time, which can be any time ranging from one minute to a few days. For purposes of generating the report 104 (as different from the purpose of calibrating the sensor device 102), the time unit used for measuring each physiological activity can vary with the physiological activity—for example, kicks can be measured for two hour time periods, rolls can be measured for three hour time periods, punches can be measured for one hour time periods, and jabs can be measured for two hour time periods.

The sensor device 102 transmits, after specific time period for each physiological activity (e.g., two hours for kicks, three hour for rolls, one hour for punches, and two hours for jabs) and to the computing server 104, a count of that physiological activity during that time period for determination of the health of the fetus within the patient 106 and the generation of the clinical report 104. Some steps performed by the sensor device 102 are also discussed below by FIG. 8.

The cloud computing server 108 receives, from the sensor device 102, a count of each physiological activity during a corresponding time period. The cloud computing server 108 determines, using those counts, a health of the fetus within the patient 106. More specifically, the cloud computing server 108 can determine whether a collective count of all physiological activities over a same time period is equal to or more than a first threshold (e.g., whether total number of distinct movements, including kicks, rolls, punches, and jabs over a time period of two hours is equal to or more than six). If such collective count is equal to or more than the first threshold, the cloud computing server 108 can record the health of the fetus as healthy. If such collective count is less than the first threshold, the cloud computing server 108 can record the health of the fetus as needing caution.

When the health of fetus is recorded as needing caution, the computing server 108 can determine whether the count of any of the physiological activities (e.g., kick, roll, punch, and jab) is equal to or more than a corresponding threshold for respective time units. If the count of any of the physiological activities is less than a corresponding threshold, the computing server 108 can record that specific activity as being low for the fetus.

If the computing server 108 determines that the health of the fetus needs caution, the computing server 108 can generate an alarm on an output device embedded on the sensor device 102. Such output device can be a display device (e.g., monitor), a speaker, a printer, any other one or more output devices, and/or any combination thereof. The alarm can be any visual display such as a pop-up window or flashing on the screen, an audio sound that can last for any preset amount of time, a print-out on a printer, any other one or more alarms, and/or any combination thereof. In some implementations, the computing server 108 can generate an alarm by way of sending an email, making a phone call, sending a social media message, and/or any combination thereof to the patient 106.

The cloud computing server 108 can then generate data for the report 104. The report 104 can include a time when the health is determined, and health as being good or needing caution. The report 104 can optionally include other measurements as well, such as a size of the fetus (as shown in FIG. 1), weight of the fetus, and/or the like, at such time. The classification of health as "good" or needing "caution" in the report 104 can be hyperlinked to other webpages that show details of counts for each physiological activity. The webpage hyperlinked to the classification of health as "caution" can further specify the particular physiological activity that has been lower than a corresponding threshold (e.g. lower than normal/expected count for that physiological activity).

Once the clinician inputs accurate user authentication on the computer 110, the cloud computing server 108 transmits the data for the clinical report 104 to the computer 110 for display thereon. Such clinician with access to the computer 110 can review the clinical report 104, and create a diagnosis and/or evaluate the patient 106 based on the clinical report 104. Further computational details of the cloud computing server 108 are discussed below with respect to FIGS. 9 and 10.

The cloud computing server 108 can update the clinical report 104 after preset intervals of time, including in real-time in some implementations. In one implementation, the cloud computing server 108 renders data for only a limited number of times, and in such case archives past time-stamped data in the clinical report 104 in a database of the cloud computing server 108. The update of the clinical report 104 in real-time can permit the clinician to review the current condition of the fetus and/or the patient 106 while also considering past time-stamped data, which enables enhanced accuracy of the diagnosis by the clinician. The preset intervals of time, in other implementations, can be 1 minute, 5 minutes, 10 minutes, 15 minutes, 30 minutes, 45 minutes, 1 hour, 2 hours, 3 hours, 5 hours, 24 hours, 1 week, 2 weeks, 1 month, or any other time interval. In some implementations, the time interval can be varied depending on the computational resources—e.g., type of controllers or processors within the cloud computing server 108, types of databases within the cloud computing server 108, available storage space within those databases, and/or any other computing resource—presently available (or alternately available within the past present amount of time, such as past one day or any other time period) at the cloud computing server 108.

The computer 110 is shown as a desktop computer. In alternate implementations, the computer 110 can be a laptop computer, a tablet computer, a phablet computer, a cellular/smart phone, and/or any other computing device. The user authentication data that the clinician inputs on the computer 110 to access the report 104 can be at least one of: username; password; personal identification number (PIN); answer to a secret question; biometric identification, including finger or thumb prints, facial recognition, retina scan or any other form of biometric data; place of authentication (e.g., current geographical location of the computer 110); time of authentication; security data obtained from an external device (e.g., security data embedded on a security key fob, one time password obtained from an email or a software application connected to a computing device of the patient 106, or the like); any other authentication data; and/or any combination thereof. Requirement for such authentication can ensure computational security of the clinical report 104, thereby keeping patient data confidential.

As noted above, the sensor device 102 has a pressure sensor to differentiate between each physiological activity by the fetus. In additional implementations, an interactive display device (not shown) can be embedded on the sensor device 102, and such display device can seek inputs from the patient 106 to confirm accuracy of identification of each detected physiological activity as specifically a kick, or specifically a roll, or specifically a punch, or specifically a jab. The sensor device 102 can have a processor and/or a hardware accelerator to effectively implement a neural network (e.g., the processor can perform some operations of the neural network in software, and the hardware accelerator can perform other operations of the neural network), which can minimize latency. Such neural network can be trained on the specific identification, by the sensor device 102 and based on the confirmatory inputs provided by the patient 106, of each separate physiological activity. The trained neural network model can be used to increase accuracy of the detections while minimizing confirmatory inputs required by the user.

Figure 2:
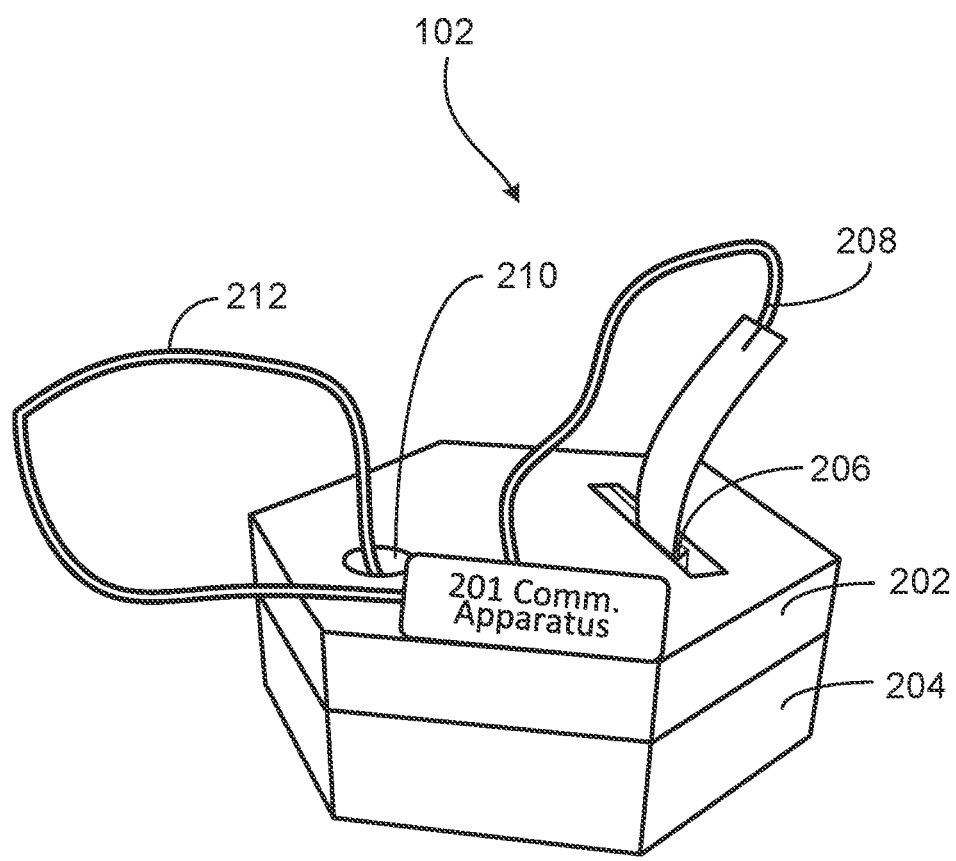
FIG. 2 illustrates a perspective view of the sensor device, showing further details of the sensor device, in accordance with some implementations of the current subject matter.

FIG. 2 illustrates a perspective view of the sensor device 102, showing further details of the sensor device 102. The sensor device 102 has a communication apparatus 201, a top cover 202, and a bottom cover 204. The top cover 202 has a first opening 206 through which a first electrical wire 208 passes, and a second opening 210 through which a second electrical wire 212 passes. The first electrical wire 208 connects a pressure sensor (as shown in FIGS. 4 and 5, and discussed in further detail below with respect to those drawings) embedded within the sensor device 102 to the communication apparatus 201. The second electrical wire 212 connects a dry electrode (as shown in FIGS. 3-5 and 7, and described in further detail below with respect to those drawings) embedded within the sensor device 102 to the communication apparatus 201.

The communication apparatus 201 can have a computer embedded therein, which can include a programmable processor, a main memory, a read only memory, a storage device, a bus that communicates with the electrical wires 208 and 212, and a transceiver that includes a transmitter for transmitting data to the computing server 108 and a receiver for receiving data from the computing server 108. In some implementations, the communication apparatus 201 can further include a communication interface.

Figure 3:
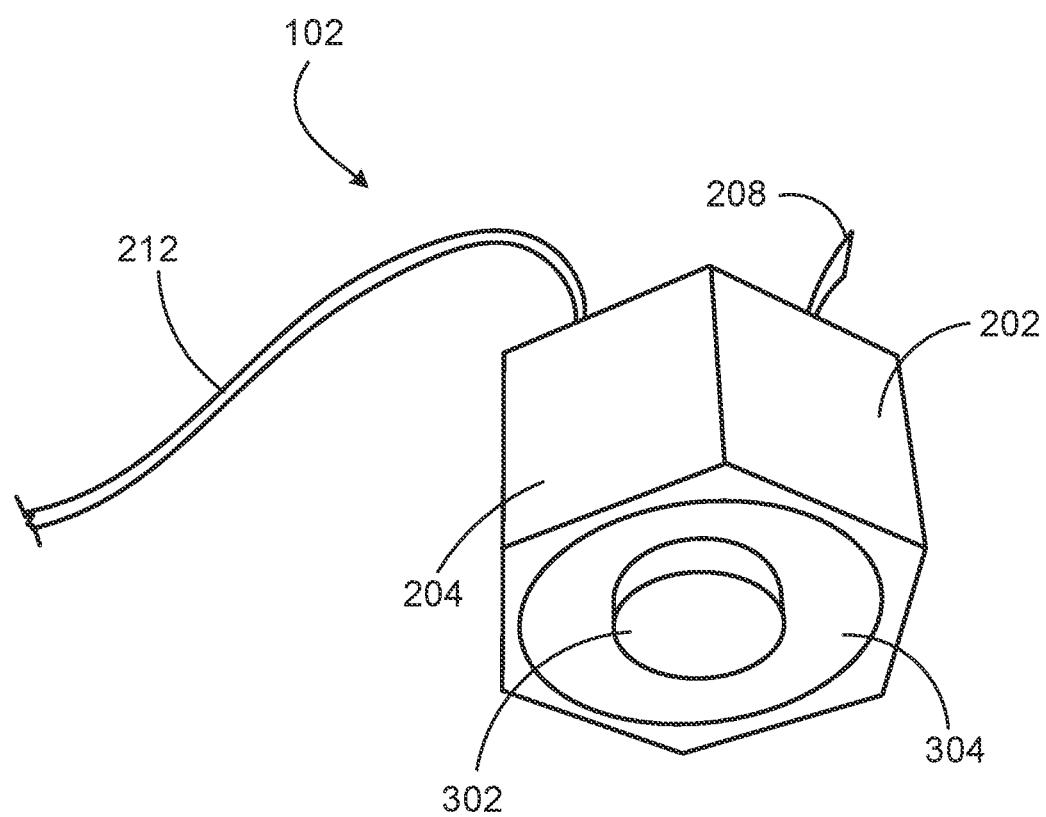
FIG. 3 illustrates another perspective view of the sensor device, in accordance with some implementations of the current subject matter.

FIGS. 3-7 illustrate various components forming the wearable sensor device 102. Specifically, FIG. 3 illustrates another perspective view of the sensor device 102. The bottom cover 204 has a dry electrode 302, which is surrounded by a surface 304 that forms a cavity. The dry electrode 302 is configured to sense signals from a belly of the patient 106 without abrasion of the skin of the patient 106 and without applying gels, fluids, or sticky and/or wet pads. The cavity formed by the surface 304 prevents the entire bottom area of bottom cover 204 from touching the belly of the patient 106, thereby rendering accuracy to acquisition of signals from the belly.

FIG. 4 illustrates an exploded view of the sensor device 102. This exploded view also shows the inner components of the sensor device 102; such inner components are visible when the sensor device 102 is either not yet assembled or disassembled. The sensor device 102 includes the top cover 202, a spring 402, a disc 404, a pressure sensor 406 that has the electrical wire 208, a top bowl 408, a bottom bowl 410, a screw 412 to mechanically connect the dry electrode 302 with the top bowl 408 and the bottom bowl 410, the dry electrode 302, and the bottom cover 204. The bottom bowl 410 has an opening 414; the dry electrode 302 has an opening 416; and the bottom cover 204 has an opening 418. The openings 414 and 416 allow the screw 412 to pass through. The opening 418 provides a passage for the dry electrode to pass through.

The top cover 202 has a cavity 420 that can tightly couple with the spring 402 by holding the spring 402. The top cover further has clips 422 that lock the top cover 202 and the bottom cover 204 together. The top surface of the pressure sensor 406 floats adjacent to the bottom surface of the disc 404, but the edge surface of the disc 404 prevents the pressure sensor 406 from disconnecting from the disc 404 when the sensor device 102 has been assembled. A top surface of the top bowl 408 has a projection (as noted in FIG. 5), which fits and locks with a bottom surface of the pressure sensor 406.

FIG. 5 illustrates another exploded view of the sensor device 102. This view additionally shows that the disc 404 is attached to a circular clip 502 designed to couple with the cavity 420. As the circular clip 502 moves with respect to the cavity 420 (i.e., as the distance between the top cover 202 and the disc 404 is varied), the compression of the spring varies, and thus the pressure applied on the pressure sensor varies. The distance between the top cover 202 and the disc 404 can be adjusted to calibrate the pressure sensor 406. The top surface of the top bowl 408 has a projection 504, which fits and locks with a bottom surface of the pressure sensor 406. The projection 504 has the shape of a square, as shown, and the bottom of the pressure sensor 406 has a corresponding shape. In an alternate implementation, the projection 504 and corresponding surface at the bottom of the pressure sensor 406 can have a circular shape so as to maximize targeted area so as to maximize the sensing ability of the sensor device 102. In yet another implementation, the projection 504 and corresponding surface at the bottom of the pressure sensor 406 can have any other shape, such as a rectangle, triangle, any polygon, any irregular shape, or any other shape.

Figure 6:
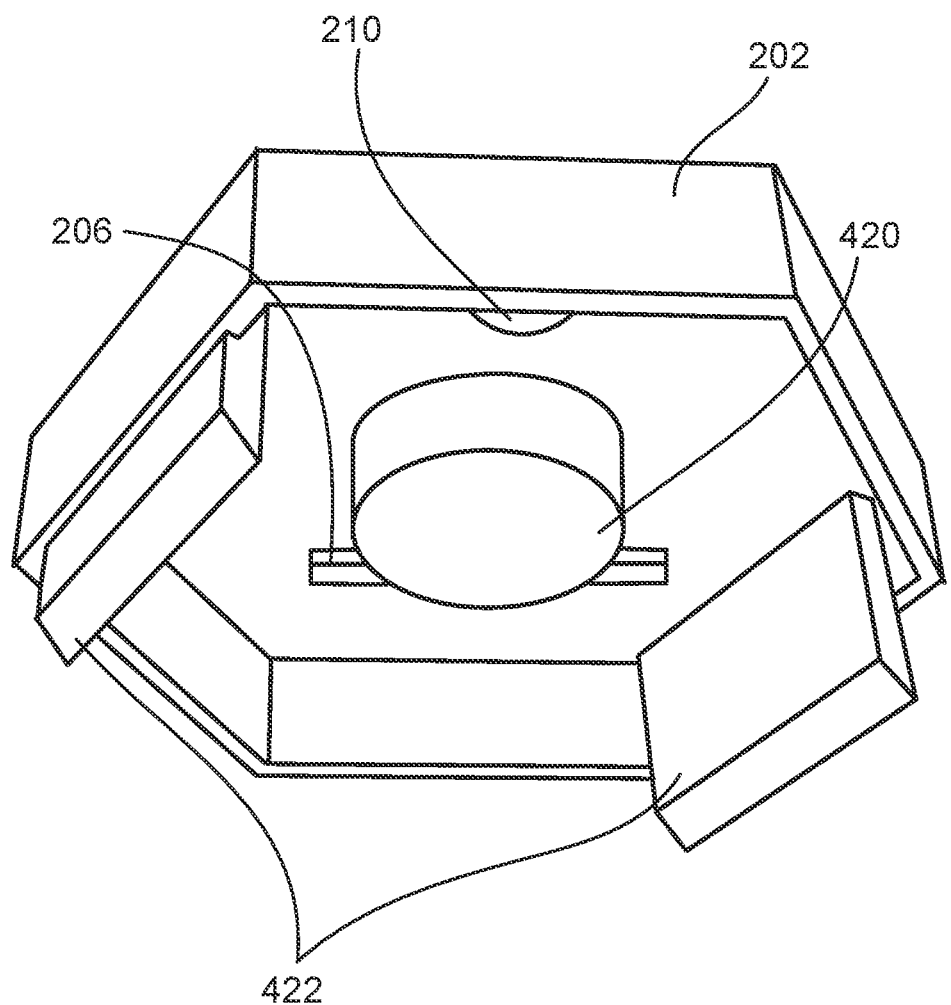
FIG. 6 illustrates another view of a top cover of the sensor device, in accordance with some implementations of the current subject matter.

FIG. 6 illustrates another view of the top cover 202.

Figure 7:
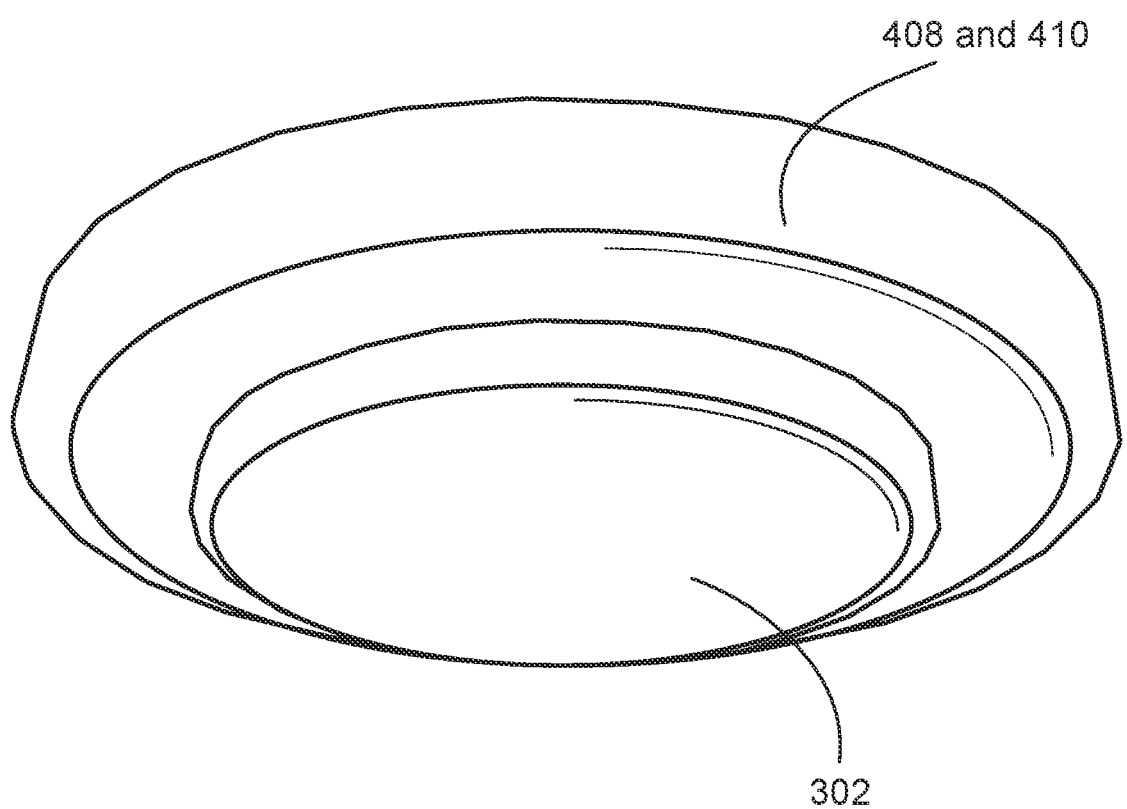
FIG. 7 illustrates a perspective view of a dry electrode of the sensor device when assembled alongside a top bowl and a bottom bowl of the sensor device, in accordance with some implementations of the current subject matter.

FIG. 7 illustrates a perspective view of the dry electrode 302 when assembled alongside the combination of the top bowl 408 and the bottom bowl 410.

Figure 8:
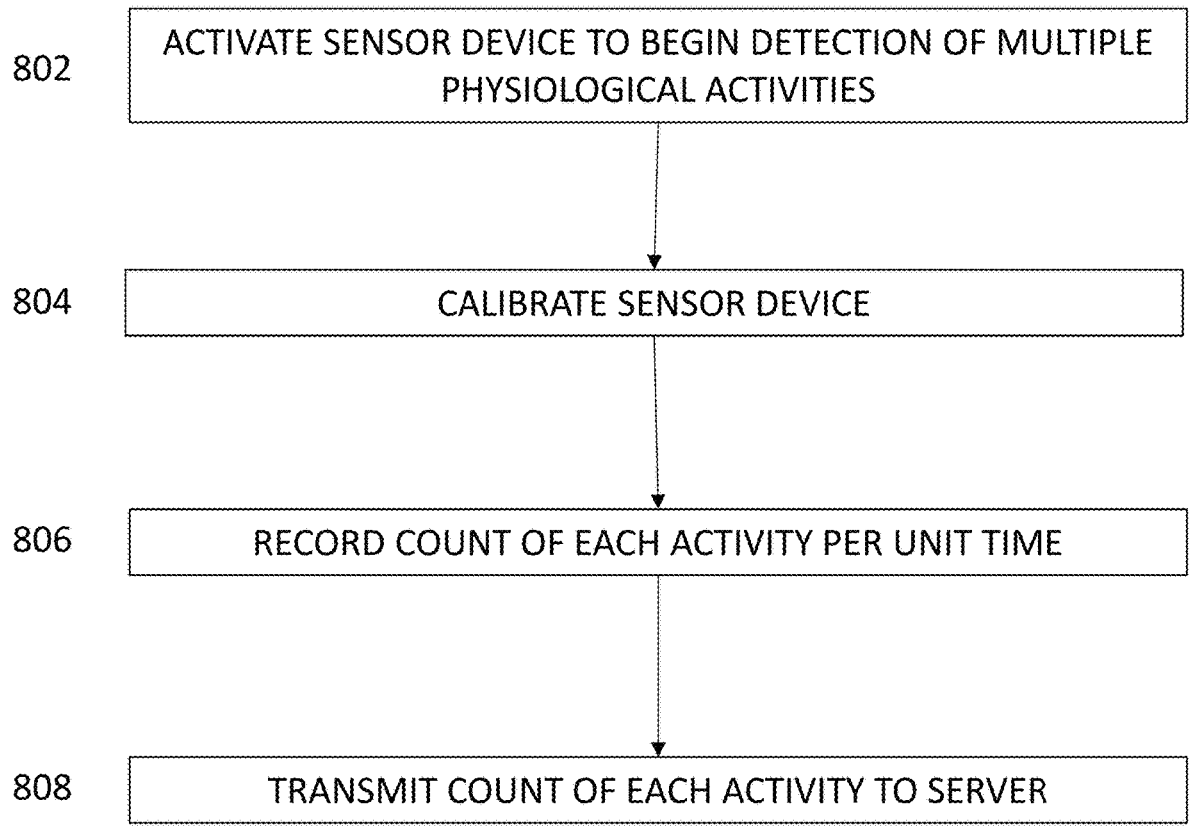
FIG. 8 is a flow diagram illustrating various steps performed by the sensor device, in accordance with some implementations of the current subject matter.

FIG. 8 is a flow diagram illustrating various steps performed by the sensor device 102. The sensor device 102 can have an electronic button that can be pressed by the patient 106 to activate, at 802, the sensor device 102. Once activated, the sensor device 102 can begin monitoring (e.g., sensing) physiological activities of the fetus within the patient 106. The sensor device 102 can receive data stored within the cloud computing server 108 so as to calibrate the sensors within the sensor device 102. The sensor device 102 can then calibrate, at 804, the sensors using such received data.

The sensor device 102 can continue to monitor the physiological activities once the sensors within the sensor device 102 have been calibrated. Such monitoring can be in real-time in one implementation where the report 104 needs to be, for example, updated in real-time. In an alternate implementation, such sensing can be performed at specific intervals to reduce or minimize computational latency. The sensor device 102 can record, at 806, a count of each physiological activity per unit time. The sensor device 102 can transmit, at 808, the count of each physiological activity to the cloud computing server 108 for determining a health condition of the fetus within the patient 106 at different time points and generation of a clinical report 104.

In some implementations, a non-transitory computer program product is described that can store instructions that, when executed by at least one programmable processor, cause the at least one programmable processor to perform operations including steps 802, 804, 806, and/or 808. In another implementation, a system is described that includes: at least one programmable processor; and a machine-readable medium storing instructions that, when executed by the at least one processor, cause the at least one programmable processor to perform operations including steps 802, 804, 806, and/or 808. In yet another implementation, an article of manufacture is described that includes computer executable instructions stored on non-transitory computer readable media, which, when executed by a computer, causes the computer to perform operations including steps 802, 804, 806, and/or 808.

Figure 9:
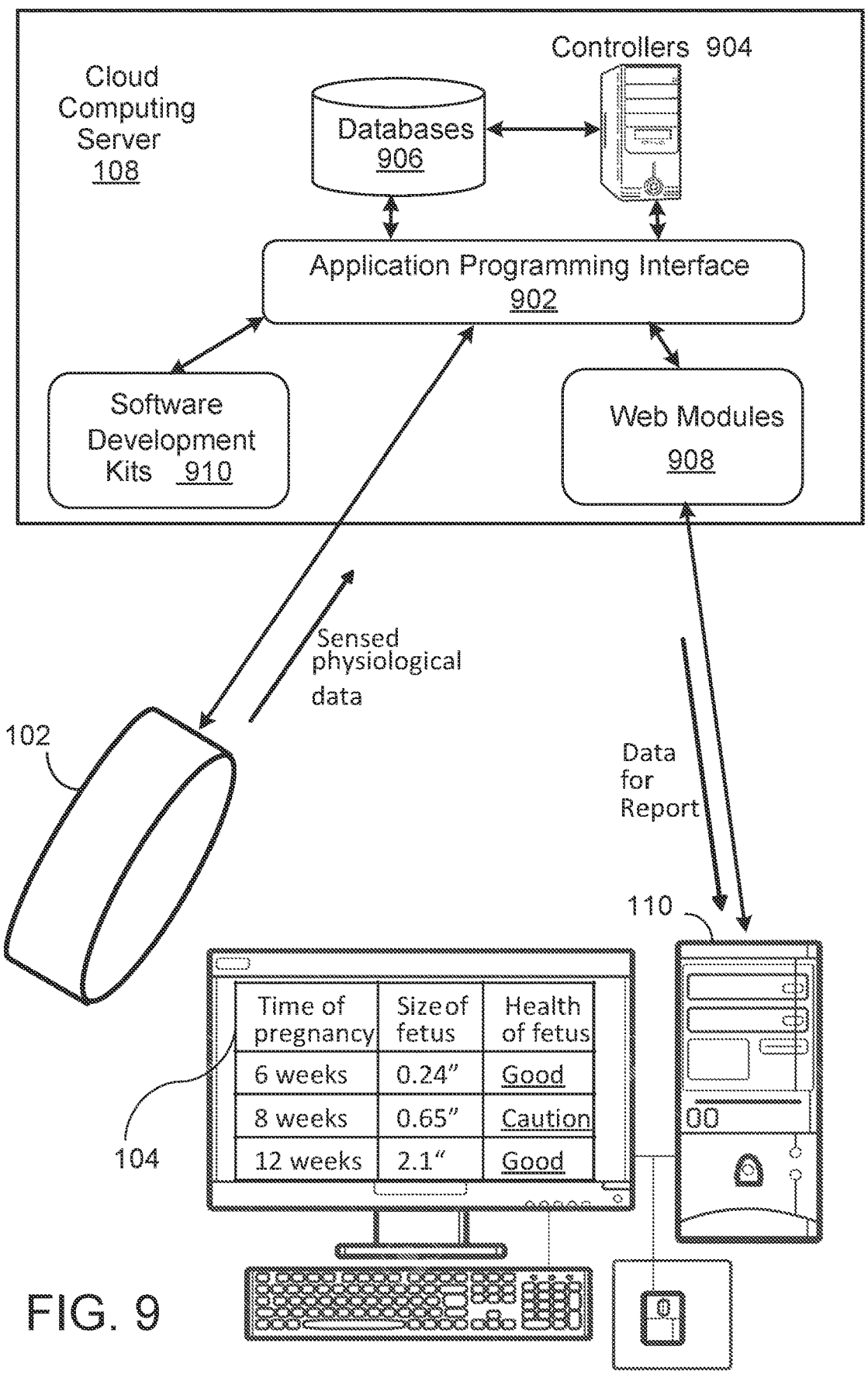
FIG. 9 illustrates further details of the cloud computing server, in accordance with some implementations of the current subject matter.

FIG. 9 illustrates details of the cloud computing server 108. The cloud computing server 108 can include an application programming interface (API) 902, controllers 904, databases 906, web modules 908, and software development kits 910.

The API 902 can receive, from the communication apparatus 201 of the sensor device 102, a count of each physiological activity. The one or more controllers 904 can determine, based on a total count for all physiological activities per unit time, a health condition of the patient 106. The one or more controllers 904 can store the health condition and related data (e.g., count for each physiological activity) in the one or more databases 906. The one or more controllers 904 can generate, using the health condition and related data, data for the report 104 indicating the health of the patient. The one or more controllers 904 can transmit—via the API 902 and one or more web modules 908 and in response to the clinician inputting user authentication data on the computer 110—the generated data to the computer 110 for display in the report 104 on the computer 110.

The API 902 can be a set of subroutine definitions, protocols, and/or tools that define method of communication between the sensor device 102 and the cloud computing server 108 and between a client-application that runs on the computer 110 to, among other things, display the clinical report 104, and the cloud computing server 108. The API 902 can ensure, for example, that the data from the sensor device 102 and the computer 110 can be read by the one or more controllers 904.

Each database 906 can be a cloud database, which can advantageously permit an easy scalability of the database 906 when required (e.g., when additional data needs to be stored, which can happen, for example, when the number of patients 106 increase beyond a threshold value). In one implementation, access to that database 906 can be provided as a service. In some implementations, the database 906 can be run on virtual machine instances. In one implementation, the database 906 can be a disk storage. In some alternate implementations, the database 906 can be a main memory (e.g., random access memory) rather than a disk storage. In those alternate implementations, access of data from the main memory can advantageously eliminate seek time when querying the data, which can provides a faster access of data, as compared to accessing data from the disk.

The web modules 908 are a back-end representation of the front-end web-based application that displays the clinical report 104 on any computer, such as the computer 110. In one implementation, one or more web modules 908 can be created by assembling servlets, JavaServer Pages (JSP) files, and static content such as Hypertext Markup Language (HTML) pages into a single deployable unit.

The software development kits (SDKs) 910 are software development tools that can be used to modify, if and when needed, the features of the application on the computer 110 that displays the clinical report 104.

The use of a cloud computing server 108 can be advantageous over a traditional server, as the cloud computing server 108 permits a quick scalability by modification of current web services and/or addition of additional web services within a few seconds. When the data received by the sensor devices 102 of one or more (including all) patients increases, additional controllers 904 or databases 906 can be added—or alternately the processing abilities of the existing controllers 904 or databases 906 can be enhanced—within a few seconds. Additionally, inclusion of API 902, controllers 904, databases 906, web modules 908, and SDKs 910 within the cloud computing server 108 can advantageously enable: a dynamic provisioning, monitoring and managing of the clinician-application that displays the clinical report 104; as well as an easy and a quick (e.g., within a few seconds) restoring of the clinician's application to a previous version of that application if and when required.

Figure 10:
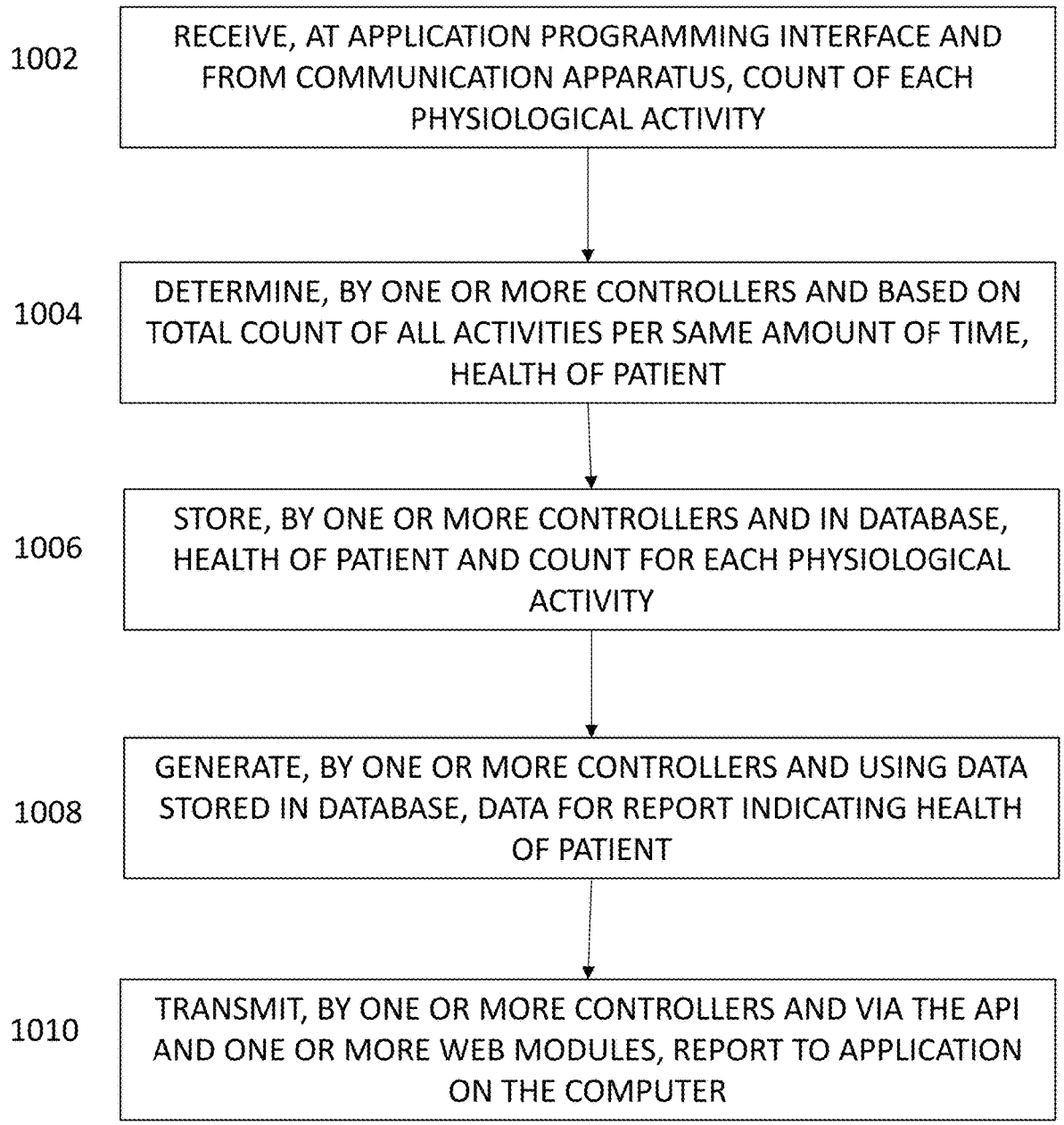
FIG. 10 is a flow diagram illustrating various steps performed by the cloud computing server, in accordance with some implementations of the current subject matter.

FIG. 10 is a flow diagram illustrating various steps performed by the cloud computing server 108. The API 902 can receive, at 1002 and from the communication apparatus 201 of the sensor device 102, a count of each physiological activity. The one or more controllers 904 can determine, at 1004 and based on a total count for all physiological activities per unit time, a health condition of the patient 106. The one or more controllers 904 can store, at 1006, the health condition and related data (e.g., count for each physiological activity) in the one or more databases 906. The one or more controllers 904 can generate, at 1008 and based on the health condition and related data, data for report indicating the health of the patient 106. The one or more controllers 904 can transmit—at 1010 and via the API 902 and one or more web modules 908 and in response to the clinician inputting user authentication data on the computer 110—the generated data to the computer 110 for display in a clinical report 104 on the computer 110.

In one implementation, a non-transitory computer program product is described that can store instructions that, when executed by at least one programmable processor, cause the at least one programmable processor to perform operations including steps 1002, 1004, 1006, 1008 and/or 1010. In another implementation, a system is described that includes: at least one programmable processor; and a machine-readable medium storing instructions that, when executed by the at least one processor, cause the at least one programmable processor to perform operations including steps 1002, 1004, 1006, 1008 and/or 1010. In yet another implementation, an article of manufacture is described that includes computer executable instructions stored on non-transitory computer readable media, which, when executed by a computer, causes the computer to perform operations including steps 1002, 1004, 1006, 1008 and/or 1010.

Figure 11:
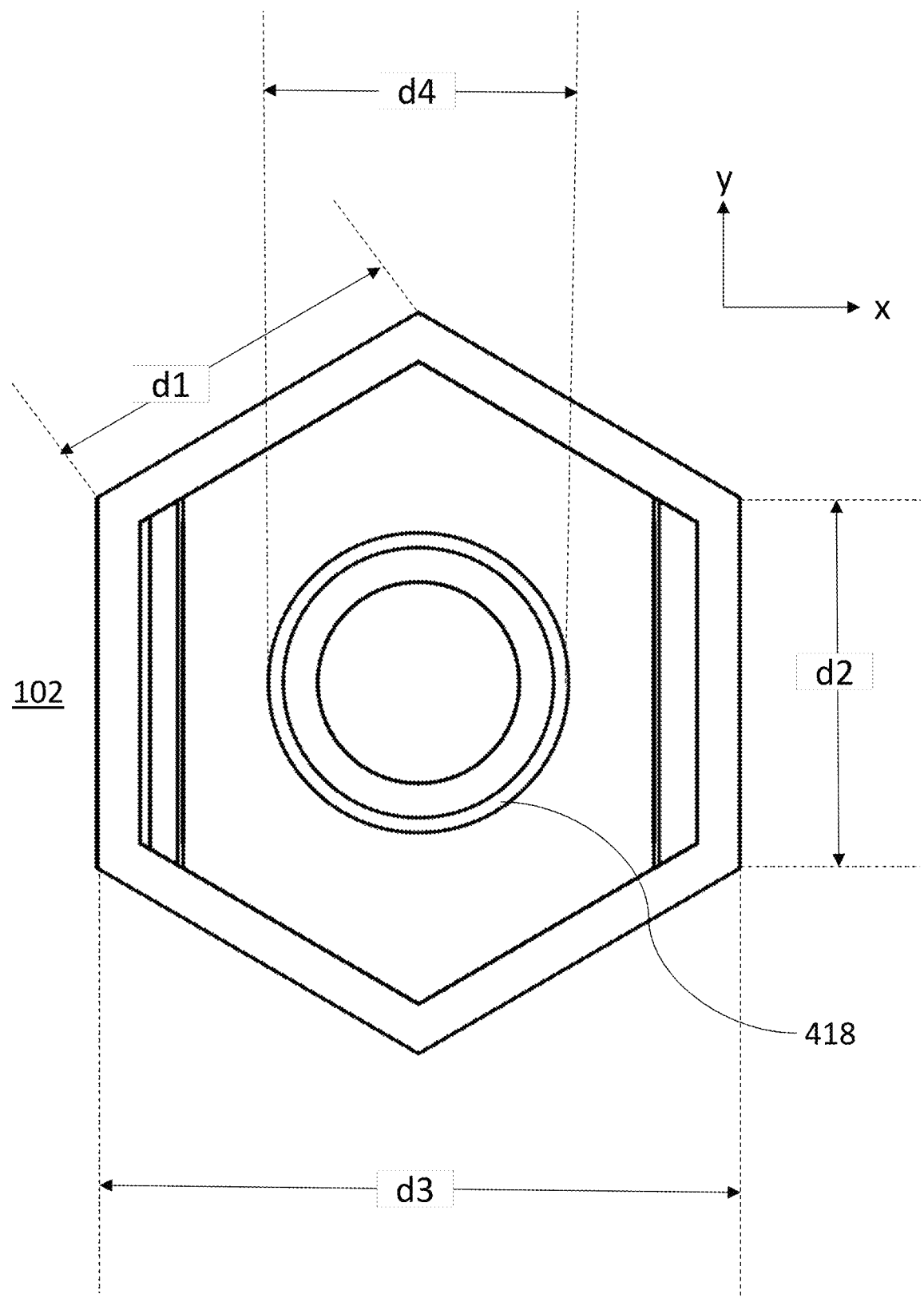
FIG. 11 illustrates some dimensions of the sensor device, in accordance with some implementations of the current subject matter.

FIG. 11 illustrates some dimensions d1, d2, d3 and d4 of the sensor device 102 shown in an x-y plane. The dimensions d1 and d2, each of which represent a side of the hexagonal shape of the sensor device 102, have a same value of 8.6547 mm. The dimension d3, which represents distance between two parallel sides of the hexagonal shape is 14.9904 mm. The opening 418 has a diameter of 7 mm. The thickness of the sensor device 102 along an axial z axis, which is perpendicular to the x-y plane, is 15 mm.

In some implementations, each side of the hexagonal shape of the sensor device 102 can have a same dimension. In other implementations, different sides of the hexagonal shape of the sensor device 102 can have different dimensions. In one implementation, each of the dimensions d1 and d2 can be any value between 7 mm and 10 mm, the dimension d3 can be any value between 13.5 mm and 16.5 mm, the dimension d4 can be any value be between 6 mm and 8 mm, and the thickness can be any value between 13.8 mm and 16.2 mm.

The dimensions d1, d2, d3, d4 and the thickness, as noted above, further clarify the compactness and portability of the sensor device 102.

Various implementations of the subject matter described herein can be realized/implemented in digital electronic circuitry, integrated circuitry, specially designed application specific integrated circuits (ASICs), computer hardware, firmware, software, and/or combinations thereof. These various implementations can be implemented in one or more computer programs. These computer programs can be executable and/or interpreted on a programmable system. The programmable system can include at least one programmable processor, which can have a special purpose or a general purpose. The at least one programmable processor can be coupled to a storage system, at least one input device, and at least one output device. The at least one programmable processor can receive data and instructions from, and can transmit data and instructions to, the storage system, the at least one input device, and the at least one output device.

These computer programs (also known as programs, software, software applications or code) can include machine instructions for a programmable processor, and can be implemented in a high-level procedural and/or object-oriented programming language, and/or in assembly/machine language. As can be used herein, the term "machine-readable medium" can refer to any computer program product, apparatus and/or device (for example, magnetic discs, optical disks, memory, programmable logic devices (PLDs)) used to provide machine instructions and/or data to a programmable processor, including a machine-readable medium that can receive machine instructions as a machine-readable signal. The term "machine-readable signal" can refer to any signal used to provide machine instructions and/or data to a programmable processor.

To provide for interaction with a user, the subject matter described herein can be implemented on a computer that can display data to one or more users on a display device, such as a cathode ray tube (CRT) device, a liquid crystal display (LCD) monitor, a light emitting diode (LED) monitor, or any other display device. The computer can receive data from the one or more users via a keyboard, a mouse, a trackball, a joystick, or any other input device. To provide for interaction with the user, other devices can also be provided, such as devices operating based on user feedback, which can include sensory feedback, such as visual feedback, auditory feedback, tactile feedback, and any other feedback. The input from the user can be received in any form, such as acoustic input, speech input, tactile input, or any other input.

The subject matter described herein can be implemented in a computing system that can include at least one of a back-end component, a middleware component, a front-end component, and one or more combinations thereof. The back-end component can be a data server. The middleware component can be an application server. The front-end component can be a client computer having a graphical user interface or a web browser, through which a user can interact with an implementation of the subject matter described herein. The components of the system can be interconnected by any form or medium of digital data communication, such as a communication network. Examples of communication networks can include a local area network, a wide area network, internet, intranet, Bluetooth network, infrared network, or other networks.

The computing system can include clients and servers. A client and server can be generally remote from each other and can interact through a communication network. The relationship of client and server can arise by virtue of computer programs running on the respective computers and having a client-server relationship with each other.

Computer program products are also described that comprise non-transitory computer readable media storing instructions, which when executed by at least one data processors of one or more computing systems, causes at least one data processor to perform operations herein. Similarly, computer systems are also described that may include one or more data processors and a memory coupled to the one or more data processors. The memory may temporarily or permanently store instructions that cause at least one processor to perform one or more of the operations described herein. In addition, methods can be implemented by one or more data processors either within a single computing system or distributed among two or more computing systems.

Although a few variations have been described in detail above, other modifications can be possible. For example, the logic flows depicted in the accompanying figures and described herein do not require the particular order shown, or sequential order, to achieve desirable results. Other embodiments may be within the scope of the following claims.

What is claimed is:

1. A method comprising:
    commencing, by a controller within a sensor device and in response to pressing of a button on the sensor device, sensing of physiological activities of a fetus from a belly of a first pregnant patient;
    calibrating, by the controller, one or more sensors within the sensor device based on historical data stored in a cloud database communicatively coupled to the controller, wherein the historical data comprises data from a previous pregnancy of the first pregnant patient, wherein the data from a previous pregnancy of the first pregnant patient were obtained by the sensor device prior to the calibration;
    determining, by the controller, counts of the physiological activities per unit time once the one or more sensors have been calibrated;
    identifying, by the controller, a type of each of the sensed physiological activities; and
    for each type of the sensed physiological activity:
        in response to an amount of time associated with the type of sensed physiological activity elapsing, transmitting, by the controller and to a cloud computing server, the counts of the type of sensed physiological activity per unit time over the amount of time for assessment of fetal health for the first pregnant patient.

2. The method of claim 1, wherein the cloud computing server is configured to generate a web-based report that comprises the assessment of fetal health for the first pregnant patient.

3. The method of claim 2, wherein the web-based report is updated in real-time.

4. The method of claim 2, wherein the web-based report is updated at time-intervals determined based on computing resources of the cloud computing server.

5. The method of claim 1, wherein the sensor device is configured to be worn on a maternity belt.

6. The method of claim 1, wherein the sensor device is configured to be a part of clothing of the first pregnant patient.

7. The method of claim 1, wherein the sensor device is portable.

8. The method of claim 1, wherein the physiological activities are fetal activities selected from the group consisting of kicks, rolls, punches, jabs and any combination thereof.

9. The method of claim 1, wherein when the historical data are available on the cloud computing server, the method comprises calibrating, by the controller, one or more sensors within the sensor device based on historical data retrieved from the cloud computing server, wherein the historical data are physiological activities of a third pregnant patient published by a standard body.

10. The method of claim 1, wherein the method comprises adjusting, based on the historical data, positioning of the sensor device.

11. The method of claim 1, wherein the method comprises determining a health of the fetus based on whether a collective count of the physiological activities over a same time period is equal to or more than a first threshold.

12. The method of claim 1, comprising generating an alarm on an output device in response to determining that the health of fetus needs attention.

13. A method comprising:
    commencing, by a controller within a sensor device and in response to pressing of a button on the sensor device, sensing of physiological activities of a fetus from a belly of a first pregnant patient;
    calibrating, by the controller, one or more sensors within the sensor device based on historical data stored in a cloud database communicatively coupled to the controller, wherein the historical data comprises data indicative of physiological activities of a second pregnant patient who is in the same stage in pregnancy;
    determining, by the controller, counts of the physiological activities per unit time once the one or more sensors have been calibrated; and
    identifying, by the controller, a type of each of the sensed physiological activities; and
    for each type of the sensed physiological activity:
        in response to an amount of time associated with the type of sensed physiological activity elapsing, transmitting, by the controller and to a cloud computing server, the counts of the type of sensed physiological activity per unit time over the predetermined amount of time for assessment of fetal health for the first pregnant patient.

14. The method of claim 13, wherein the physiological activities are fetal activities selected from the group consisting of kicks, rolls, punches, jabs and any combination thereof.

15. The method of claim 13, wherein when the historical data are available on the cloud computing server, the method comprises calibrating, by the controller, one or more sensors within the sensor device based on historical data retrieved from the cloud computing server, wherein the historical data are physiological activities of a third pregnant patient published by a standard body.

16. The method of claim 13, wherein the method comprises adjusting, based on the historical data, positioning of the sensor device.

17. The method of claim 13, wherein the method comprises determining a health of the fetus based on whether a collective count of physiological activities over a same time period is equal to or more than a first threshold.

18. The method of claim 17, comprising generating an alarm on an output device in response to determining that the health of fetus needs attention.

* * * * *